United States Patent
Cheng et al.

(10) Patent No.: US 9,771,609 B2
(45) Date of Patent: Sep. 26, 2017

(54) ELECTRODE FOR URIC ACID AND METHOD OF PRODUCING THE SAME

(71) Applicant: Chung Yuan Christian University, Tao-Yuan (TW)

(72) Inventors: Chean-Yeh Cheng, Toa-Yuan (TW); Chi-Ying Kao, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 481 days.

(21) Appl. No.: 14/460,750

(22) Filed: Aug. 15, 2014

(65) Prior Publication Data
US 2015/0322475 A1 Nov. 12, 2015

(30) Foreign Application Priority Data
May 8, 2014 (TW) .............................. 103116452 A (51) Int. Cl.
*C12Q 1/26* (2006.01)
*C12Q 1/58* (2006.01)
(Continued)

(52) U.S. Cl.
CPC ............ *C12Q 1/004* (2013.01); *C12Q 1/005* (2013.01); *G01N 27/3277* (2013.01); *G01N 27/3271* (2013.01)

(58) Field of Classification Search
CPC . C12Q 1/001–1/008; C12Q 1/25; C12Q 1/58; C12Q 1/62; G10N 27/327–27/3335
(Continued)

(56) References Cited

U.S. PATENT DOCUMENTS 5,834,273 A * 11/1998 Futatsugi ............. C12N 9/0046
                                                               435/177
6,165,335 A * 12/2000 Lennox ................. C12Q 1/003
                                                               204/403.01
(Continued)

FOREIGN PATENT DOCUMENTS

CN          103454328 A      12/2013
JP          2008129001 A     6/2008
(Continued)

OTHER PUBLICATIONS

Ojani, Reza, et al. "A Highly Sensitive Electrochemical Sensor for Simultaneous Detection of Uric Acid, XAnthine and Hypoxanthine Based on Poly (L-methionine) Modified Glassy Carbon Electrode," Sensors and Actuators B Chemical, vol. 188 (2013), pp. 621-630.
(Continued)

*Primary Examiner* — Bach Dinh
(74) *Attorney, Agent, or Firm* — Donald E. Stout; Stout, Uxa & Buyan, LLP (57) ABSTRACT

Embodiments of this invention disclose new second generation uric acid-sensing electrodes at least characterized by chemically bonding both uricase and the redox mediator to an electrode. The produced electrodes can be long-term stably used without losing activity. The developed electrode has been successfully applied for the analysis of uric acid (UA) in healthy human urine specimens which exhibits very good analysis accuracy and precision without too much interference. Therefore, the developed electrodes have the potential for clinical applications.

4 Claims, 9 Drawing Sheets

(51) Int. Cl.
*C12Q 1/62* (2006.01)
*G01N 27/327* (2006.01)
*C12Q 1/00* (2006.01)

(58) Field of Classification Search
USPC .................................. 204/403.01–403.15
See application file for complete search history.

(56) References Cited

U.S. PATENT DOCUMENTS

| | | | |
|---|---|---|---|
| 2002/0039743 A1* | 4/2002 | Hashimoto | C12Q 1/6825 435/6.11 |
| 2004/0149578 A1* | 8/2004 | Huang | G01N 27/3272 204/403.01 |
| 2010/0311143 A1* | 12/2010 | Cheng | C12Q 1/001 435/177 |

FOREIGN PATENT DOCUMENTS

| JP | 2008215887 A | 9/2008 |
|---|---|---|
| JP | 2009069085 A | 4/2009 |
| TW | 201120442 A | 6/2011 |
| TW | I408371 B | 9/2013 |

OTHER PUBLICATIONS

Erden, P. E., Kiliç, E., 2013. Talanta 107, 312-323.
Arora, K., Sumana, G., Saxena, V., Gupta, R.K., Gupta, S.K., Yakhmi, J.V., Pandey, M.K., Chand, S., Malhotra, B.D., 2007. Anal. Chim. Acta 594, 17-23.
Jindal, K., Tomar, M., Gupta V., 2012. Biosens. Bioelectron. 38, 11-18.
Kanyong, P., Pemberton, R.M., Jackson, S.K., Hart, J.P., 2012. Anal. Biochem. 428, 39-43.
Rawal, R., Chawla, S., Chauhan, N., Dahiya, T., Pundir, C.S., 2012. Int. J. Biol. Marcromol. 50, 112-118.
Zhao, Y., Yan, X., Kang, Z., Lin, P., Fang, X., Lei, Y., Ma, S., Zhang, Y., 2013. Microchim. Acta 180, 759-766.
Dey, R.S., Raj, C.R., 2013. ACS Appl. Mater. Interfaces 5, 4791-4798.
Miland, E., Miranda Ordieres, A.J., Tuñón Blanco, P., Smyth, M.R., 1996. Talanta 43, 785-796.
Dutra, R.F., Moreira, K.A., Oliveira, M.I.P., Araújo, A.N., Montenegro, M.C.B.S., Filho, J.L.L., Silva, V.L., 2005. Electroanalysis 17, 701-705.
Chaki, N.K., Vijayamohanan, K., 2002. Biosens. Bioelectron. 17, 1-12.
Sun, Z., Fu, H., Den, L., Wang, J., 2013. Anal. Chim. Acta 761, 84-91.
Kuwabata, S., Nakaminami, T., Ito, S.-I., Yoneyama, H., 1998. Sens. Actuators B 52, 72-77.
Luo, Y.-C., Do, J.-S., Liu, C.-C., 2006. Biosens. Bioelectron. 22, 482-488.
Ahuja, T., Tanwar, V.K., Mishra, S.K., Kumar, D., Birada, A.M., Rajesh, 2011. J. Nanosci. Nanotechnol. 11, 4692-4701.
Chauhan, N., Pundir, C.S., 2011. Anal. Biochem. 413, 97-103.
Iveković, D., Japec, M., Solar, M., Živković, N., 2012. Int. J. Electrochem. Sci. 7, 3252-3264.
Akyilmaz, E., Sezgintürk, M.K., Dinçkaya, E., 2003. Talanta 61, 73-79.
Cete, S., Yasar, A., Arslan, F., 2006. Artif. Cells Blood Substit. Biotechnol. 34, 367-380.
Cheng, C., Chang, K.-C., Pijanowska, D.G., 2012. J. Electroanal. Chem. 666, 32-41.
Huang, Y., Bu, L., Wang, W., Qin, X., Li, Z, Huang, Z., Fu, Y., Su, X., Xie, Q., Yao, S., 2013. Sens. Actuators B 177, 116-123.
Piermarini, S., Migliorelli, D., Volpe, G., Massoud, R., Pierantozzi, A., Cortese, C., Palleschi, G., 2013. Sens. Actuators B 179, 170-174.
Cheanyeh Cheng et al., "Glucose and Uric Acid Enzyme Electrode Biosensor," Chemistry (The Chinese Chemical Society, Taipei), vol. 7, No. 3, pp. 195-203.
Office Action Dated Jul. 14, 2015 in corresponding Taiwan Patent Application No. 103116452.

* cited by examiner

ELECTRODE FOR URIC ACID AND METHOD OF PRODUCING THE SAME

CROSS-REFERENCE TO RELATED APPLICATIONS

The entire contents of Taiwan Patent Application No. 103116452, filed on May 8, 2014, from which this application claims priority, are incorporated herein by reference.

BACKGROUND OF THE INVENTION

1. Field of the Invention

The present invention relates to electrodes for detecting uric acid and their producing methods.

2. Description of Related Art

Commonly found in urine and blood, uric acid (UA) is the major end product of purine metabolism in human body. In healthy people, the uric acid level in serum is in the range of 0.24-0.52 mM and is in the range of 0.214-4.40 mM in urine. High uric acid concentration accumulated in serum or urine that exceeds the normal level leads hyperuricemia and induces gout, Lesch-Nyhan syndrome, and renal diseases. Therefore, it is important to monitor uric acid in serum or urine regularly for precaution, diagnosis, and treatment of those diseases caused by high concentration of uric acid.

The analytical methods for uric acid include spectrophotometry, enzymatic method, high performance liquid chromatography (HPLC), liquid chromatography-mass spectrometry (LC-MS), capillary electrophoresis, chemiluminescence, fluorescence, phosphorescence, and electrochemical methods. But these methods generally involve tedious separation procedure, need expensive instrument, and lack specificity. Therefore, there is a great interest in developing a method that is specific, simple, easy operation, fast, and low cost for uric acid analysis. The enzyme-based sensor electrode biosensor which allows direct, specific, rapid, sensitive, and inexpensive measurement of uric acid fulfills these criteria. The use of uricase (urate oxidase, $UO_x$) for detecting uric acid can be traced back to the work of John and Bulger in 1941 [1].

To set up a stable long-term reusable uricase electrode, the immobilization of uricase on the electrode is the most important factor. There are many enzyme immobilization methods such as the physical adsorption method [2-7], the entrapment method [8-9], the self-assembled monolayer (SAM) method [10-11], the cross-linking method [12-13], and the covalent chemical bonding method [14-15]. Wherein the simplest physical adsorption subjects the problem of easily peeled off from the electrode that causes poor electrode life. There is similar problem with the entrapment method. Although the self-assembly monolayer method exhibits many merits, the long-term application is still limited. Therefore, the cross-linking method or the covalent chemical bonding method could be the ideal method for uricase immobilization to enhance the electrode performance and shelf life.

The electrode material also plays very important role for the enzyme sensor electrode which closely related to the enzyme immobilization, current conduction, and electrode fabrication costs. Metals and non-metal carbon are the two major categories. Modified metal electrodes such as zinc oxide coated gold electrode [6], the multi-walled carbon nanotube (MWCNT) modified gold electrode [15], carboxylated MWCNT and polyaniline (PANI) conducting polymer modified gold electrode [5], CuO film modified platinum electrode [3], and gold nanoparticles (AuNPs) over SAM 3-aminopropyltriethoxysilane (APTES) coated indium tin oxide (ITO) electrode [14] have been extensively used nowadays for uricase electrode. Since metal electrodes are generally expensive, carbon-based non-metallic electrodes has been gradually more interested by researchers for fabricating uricase electrode, for examples, self-assembled $UO_x$ mixed thionine-graphene oxide hybrid nanosheets on glassy carbon electrode [11], graphite disc electrode modified with Prussian blue-$Ni^{2+}$ film [16], sandwich format amperometric screen-printed carbon electrode [4], ferrocene modified grapheme oxide screen printed electrode (SPE) [7], and screen printed Ir-modified carbon electrode [13].

Uric acid is an electroactive compound that can be easily oxidized at the electrode by $UO_x$ in aqueous solution to produce allantoin, $H_2O_2$, and $CO_2$ [17]:

The produced $H_2O_2$ can be detected by its oxidation at the surface of working electrode.

However, the required electrochemical oxidation potential for $H_2O_2$ is usually high (>0.40 V) which leads other electroactive species such as ascorbic acid also oxidized in the solution to interfere the uric acid analysis. One of the approaches to solve this problem is the use of redox mediator for substituting $O_2$ to decrease the oxidation potential of uric acid to avoid the unnecessary interferences. In the meantime, the variation of atmospheric pressure during the electrochemical measurements which affects the accuracy of analysis can also be avoided. Recently, ferrocene and its derivatives have been used as a redox mediator in many applications. For instances, electropolymerization of pyrrole on Pt electrode surface containing ferrocene as a redox mediator was carried out to form a polymer film which was used to immobilized $UO_x$ for the determination of uric acid in biological fluids [17]; ferrocene carboxaldehyde was chemical bound to graphene oxide and coated over SPE to immobilize $UO_x$ for the determination of uric acid in serum [7].

In addition, the previous application (application Ser. No. 12/421,565) of the inventors provided an enzyme electrode having good performance.

REFERENCES

[1] Erden, P. E., Kiliçc, E., 2013. Talanta 107, 312-323. [2] Arora, K., Sumana, G., Saxena, V., Gupta, R. K., Gupta, S. K., Yakhmi, J. V., Pandey, M. K., Chand, S., Malhotra, B. D., 2007. Anal. Chim. Acta 594, 17-23. [3] Jindal, K., Tomar, M., Gupta V., 2012. Biosens. Bioelectron. 38, 11-18. [4] Kanyong, P., Pemberton, R. M., Jackson, S. K., Hart, J. P., 2012. Anal. Biochem. 428, 39-43. [5] Rawal, R., Chawla, S., Chauhan, N., Dahiya, T., Pundir, C. S., 2012. Int. J. Biol. Marcromol. 50, 112-118. [6] Zhao, Y., Yan, X., Kang, Z., Lin, P., Fang, X., Lei, Y., Ma, S., Zhang, Y., 2013. Microchim. Acta 180, 759-766. [7] Dey, R. S., Raj, C. R., 2013. ACS Appl. Mater. Interfaces 5, 4791-4798. [8] Miland, E., Miranda Ordieres, A. J., Tuñón Blanco, P., Smyth, M. R., 1996. Talanta 43, 785-796. [9] Dutra, R. F., Moreira, K. A., Oliveira, M. I. P., Araújo, A. N., Montenegro, M. C. B. S., Filho, J. L. L., Silva, V. L., 2005. Electroanalysis 17, 701-705. [10] Chaki, N. K., Vijayamohanan, K., 2002. Biosens. Bioelectron. 17, 1-12. [11] Sun, Z., Fu, H., Den, L., Wang, J., 2013. Anal. Chim. Acta 761, 84-91. [12] Kuwabata, S., Nakaminami, T., Ito, 5.4., Yoneyama, H., 1998. Sens. Actuators B 52, 72-77. [13] Luo, Y.-C., Do, J.-S., Liu, C.-C., 2006. Biosens. Bioelectron. 22, 482-488. [14] Ahuja, T., Tanwar, V. K., Mishra, S. K., Kumar, D., Birada, A. M., Rajesh, 2011. J. Nanosci. Nanotechnol. 11, 4692-4701. [15] Chauhan, N., Pundir, C. S., 2011. Anal. Biochem. 413, 97-103. [16] Iveković, D., Japec, M., Solar, M., Živković, N., 2012. Ent. J. Electrochem. Sci. 7, 3252-3264. [17] Akyilmaz, E., Sezgintürk, M. K., Dinç-kaya, E., 2003. Talanta 61, 73-79. [18] Cete, S., Yasar, A., Arslan, F., 2006. Artif. Cells Blood Substit. Biotechnol. 34, 367-380. [19] Cheng, C., Chang, K.-C., Pijanowska, D. G., 2012. J. Electroanal. Chem. 666, 32-41. [20] Huang, Y., Bu, L., Wang, W., Qin, X., Li, Z, Huang, Z., Fu, Y., Su, X., Xie, Q., Yao, S., 2013. Sens. Actuators B 177, 116-123. [21] Piermarini, S., Migliorelli, D., Volpe, G., Massoud, R., Pierantozzi, A., Cortese, C., Palleschi, G., 2013. Sens. Actuators B 179, 170-174.

SUMMARY OF THE INVENTION

In one general aspect, the present invention relates to electrodes for detecting uric acid and method of producing the electrodes.

According to an embodiment of this invention, a method is provided for producing an electrode to detect uric acid and comprises the steps of: providing a metal substrate; forming a gold surface on a surface of the metal substrate and thus forming an electrode; modifying the gold surface by L-methionine to covalently bond the gold particles on the gold surface and a methylsulfanyl group of L-methionine, thereby forming a first modified electrode with a first modified surface; covalently bonding a redox mediator having an aldehyde group to an amino group of the L-methionine and thus resulting in a Schiff base, thereby forming a second modified electrode with a second modified surface; modifying the second modified surface by N,N'-dicyclohexylcarbodiimide, a carboxyl group of the L-methionine and N,N'-dicyclohexylcarbodiimide forms covalent bond, thereby forming a third modified electrode with a third modified surface; and contacting the third modified surface with a uricase, an amide bond being formed between a carboxyl group of L-methionine of the third modified surface and the uricase, thereby forming a fourth modified electrode with a fourth modified surface.

According to another embodiment of this invention, an electrode is provided for detecting uric acid and comprises: a substrate having a metal surface; a gold surface formed on at least a portion of the metal surface; an L-methionine binding to the gold surface through its methylsulfanyl group; a redox mediator containing an aldehyde group, wherein the redox mediator and an amino group of the L-methionine form a Schiff base; and a uricase binding to the L-methionine through a peptide-coupling reagent with a diimide structure, wherein the uricase and the peptide-coupling reagent form an amide bond.

BRIEF DESCRIPTION OF THE DRAWINGS

FIGS. 4A-4E show the long-term stability and reusability of the developed electrode by the present invention, and the long-term stability and reusability are respectively demonstrated with the five performance parameters: FIG. 4C, the LOD.

DETAILED DESCRIPTION OF THE PREFERRED EMBODIMENT

Reference will now be made in detail to those specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations and components are not described in detail in order not to unnecessarily obscure the present invention. While drawings are illustrated in detail, it is appreciated that the quantity of the disclosed components may be greater or less than that disclosed, except where expressly restricting the amount of the components.

Figure 1:
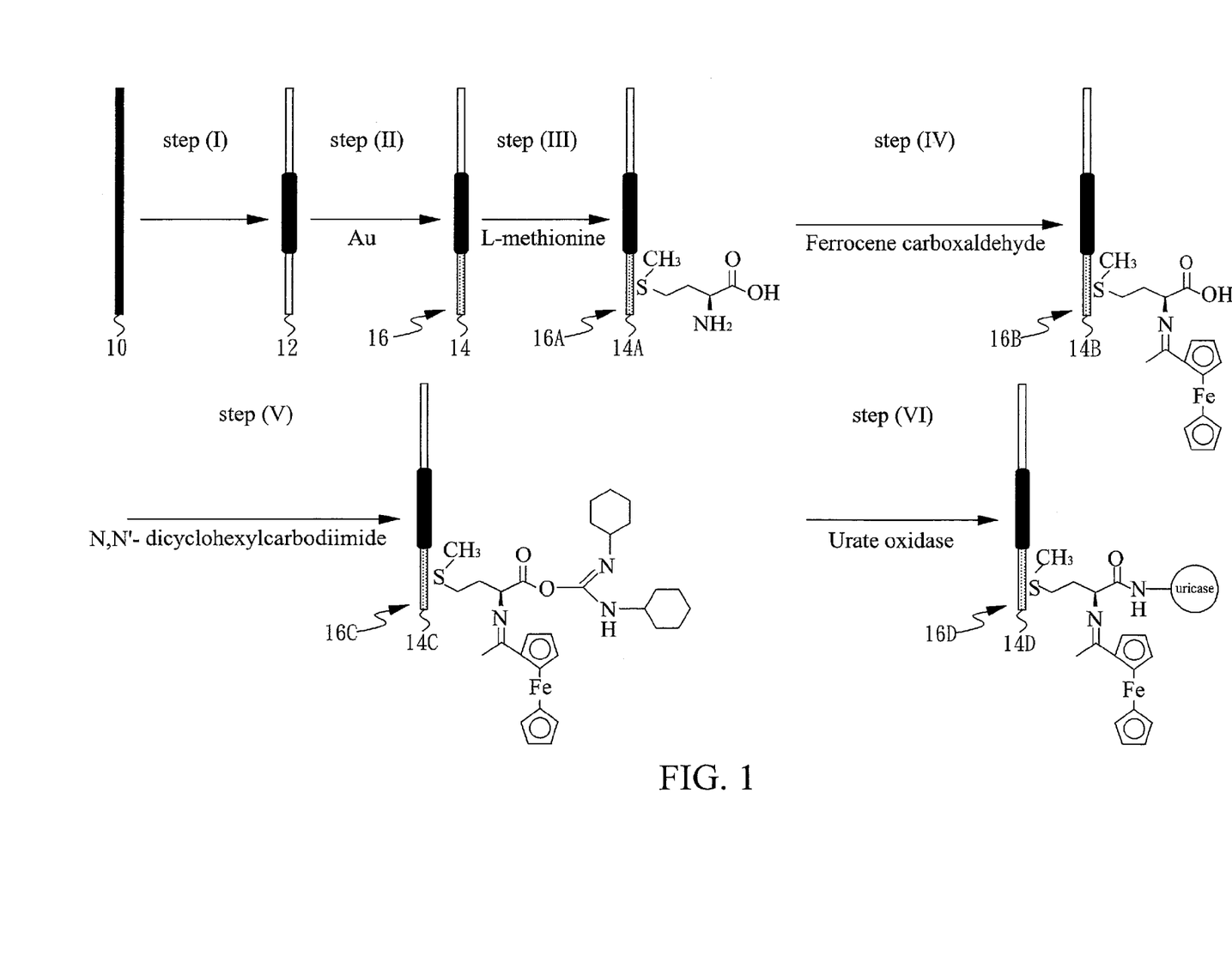
FIG. 1 is a schematic diagram showing a step by step method to produce a uric acid-sensing electrode according to a preferred embodiment of the present invention.

FIG. 1 shows a method for forming a uric acid biosensor, such as a uric acid detection electrode according to a preferred embodiment of the present invention. The method comprises the following six steps. In step (I), three centimeters of enameled copper wire 10 were cut from the reel and 0.8 cm outer polyimide coat of each end of this wire 10 was scratched and sandpapered with knife and coarse sandpaper, respectively, to expose a copper wire surface 12.

In step II, the copper wire surface 12 was immersed into a solution containing tetrachloroaurate ions at 28° C. with an applied voltage of 2.0 V for 3 h, so as to deposit gold particles on one end of the exposed copper wire surface 12, resulting in an electrode 16 with a gold surface 14. The electrode 16 was then rinsed with water to remove the residuals. In step III, the electrode 16 was immersed in a 20.0 mM L-methionine solution for 1 h at 25° C. to covalently bind the gold particles with the methylsulfanyl group of L-methionine, resulting in a first modified electrode 16A with a first modified surface 14A. The first modified electrode 16A was then thoroughly rinse with deionized distilled water to remove physically adsorbed L-methionine. In step IV, the first modified electrode 16A with the first modified surface 14A was immersed in 20.0 mM ferrocene carboxaldehyde (FcAld, dissolved in EtOH/HCl, 99.5/0.5, v/v) at 75° C. for 1 h to chemically bind FcAld via Schiff base with the amino group of L-methionine, resulting in a second modified electrode 16B with a second modified surface 14B. Thereafter, the second modified electrode 16B was rinsed with deionized distilled water at the same temperature, 75° C. In step V, the second modified electrode 16B electrode was immersed in 20.0 mM N,N'-dicyclohexylcarbodiimide (DCC) methanol solution for 1 h at 40° C. to chemically bind DCC through an amide bond with the carboxyl group of L-methionine, resulting in a third modified electrode 16C with a third modified surface 14C. The unreacted DCC then was removed by washing with methanol and deionized distilled water at 40° C. In step VI, the third modified electrode 16C was dipped in 50.0 μM uricase solution which was prepared with 0.1 M pH 7.0 sodium phosphate buffer (NaPB) at 25° C. for 24 h to chemically bind uricase to the carboxyl group of L-methionine by substituting reaction, resulting in a fourth modified electrode 16D with a fourth modified surface 14D. The fourth modified electrode 16D is the finished electrode for uric acid detection and was stored in 0.1 M pH 7.0 NaPB at 4° C. for subsequent experiments.

Modifications may be made on the above-mentioned embodiment. For example, the copper may be replaced by other metal materials, and Step (IV) may be performed after step (V) or step (VI). In addition, the substrate may be rod-shaped, slice-shaped, or other configurations instead of a wire configuration.

Other methods such as deposition, ink-inject, or screen-printing method may be employed for forming the gold surface 12. Other amino acids including an amino group, a carboxyl group, and a thiol group in the side chain, may replace L-methionine, but the performance of the formed electrodes needs to be investigated. Other peptide coupling reagents with a diimide structure may replace N,N'-dicyclohexylcarbodiimide, but the performance of the formed electrodes needs also to be investigated. And other mediators containing an aldehyde group may replace ferrocene carboxaldehyde. In addition, the temperature and the concentration of the solutions used in the above-mentioned steps may also be changed.

Characterization of Uric Acid-Sensing Electrode by FTIR

Figure 2A:
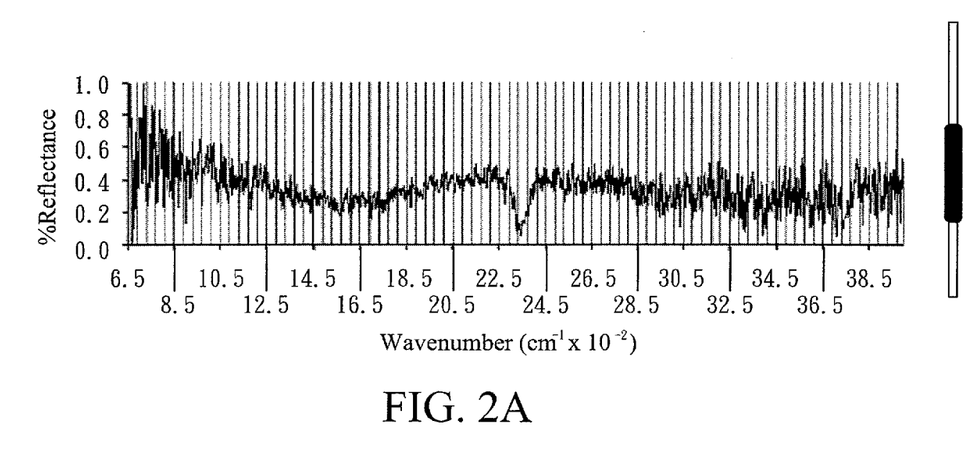
FIGS. 2A-2G step by step shows the Fourier transform infrared (FTIR) spectroscopies of the produced uric acid-sensing electrode of the preferred embodiment.
Figure 2B:
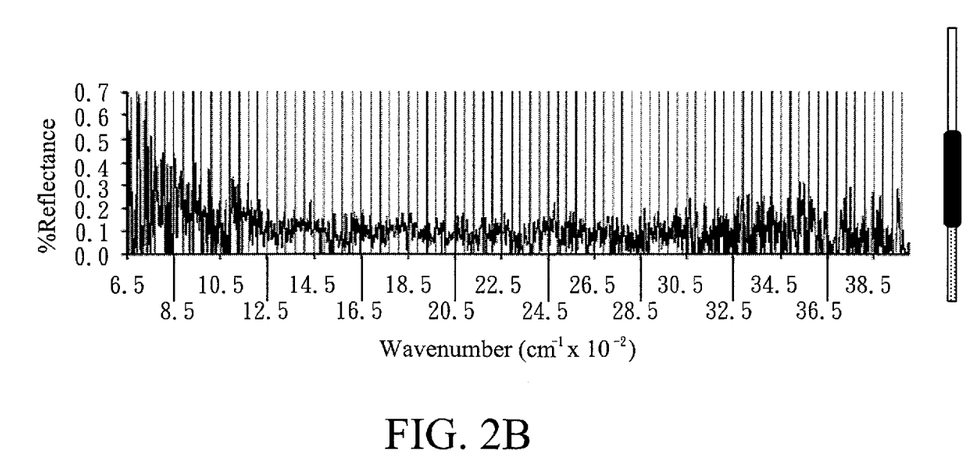
Figure 2C:
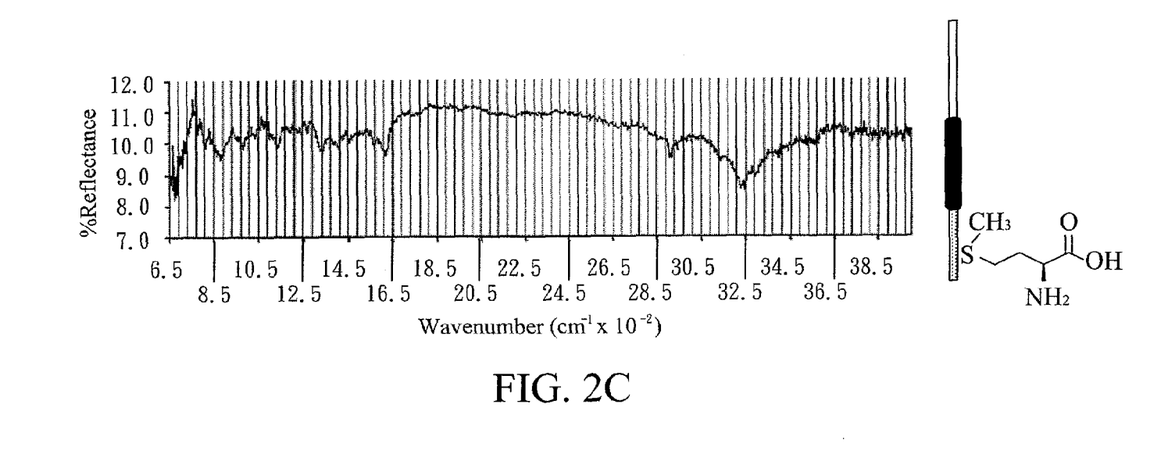
Figure 2D:
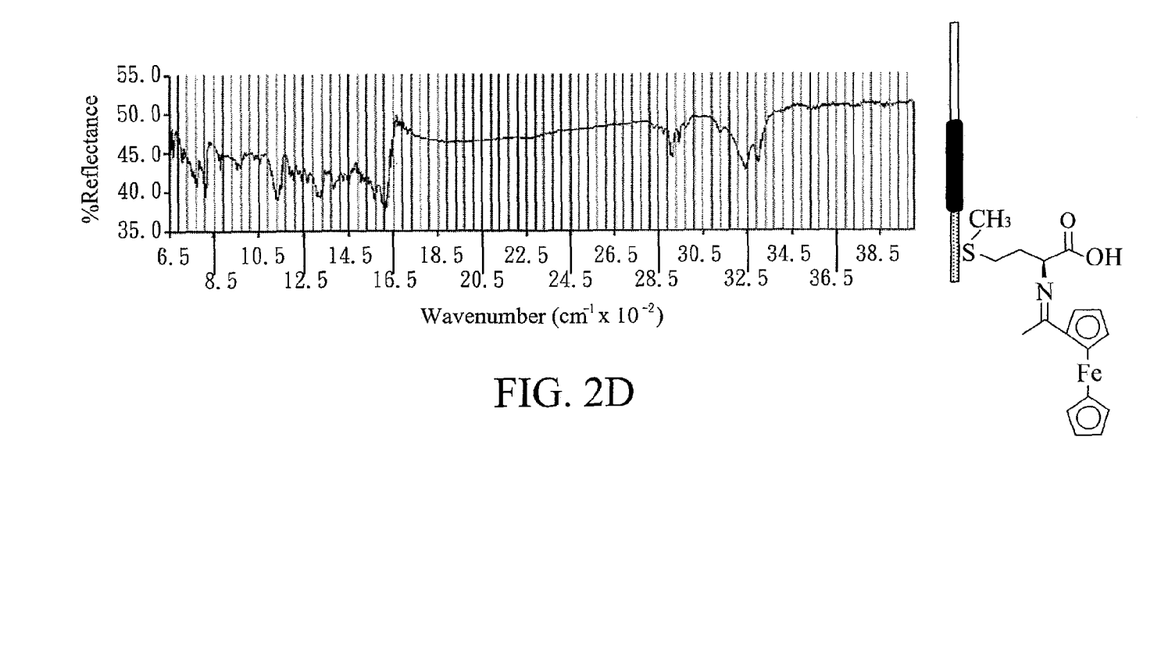
Figure 2E:
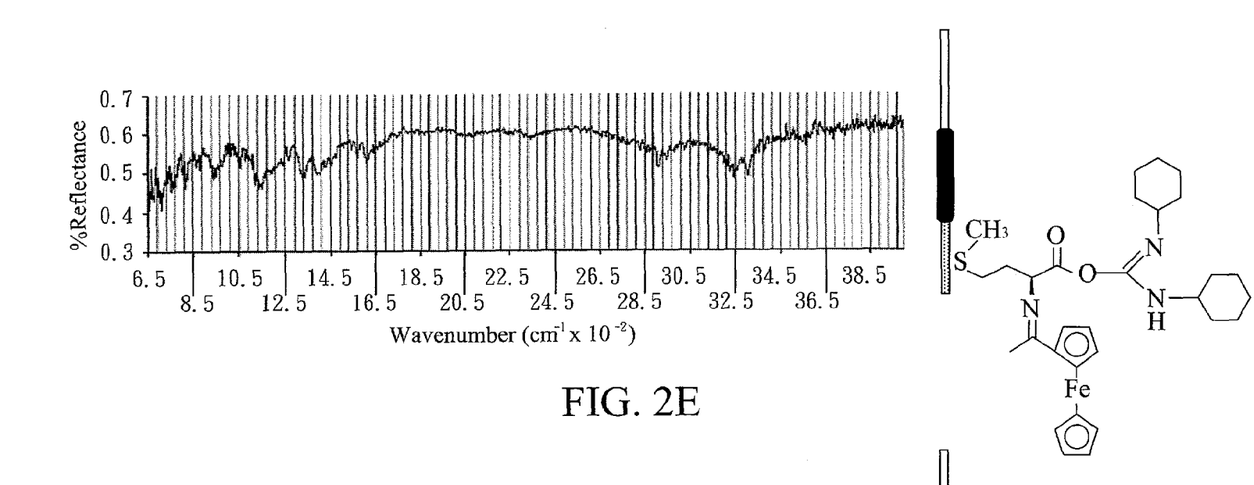
Figure 2F:
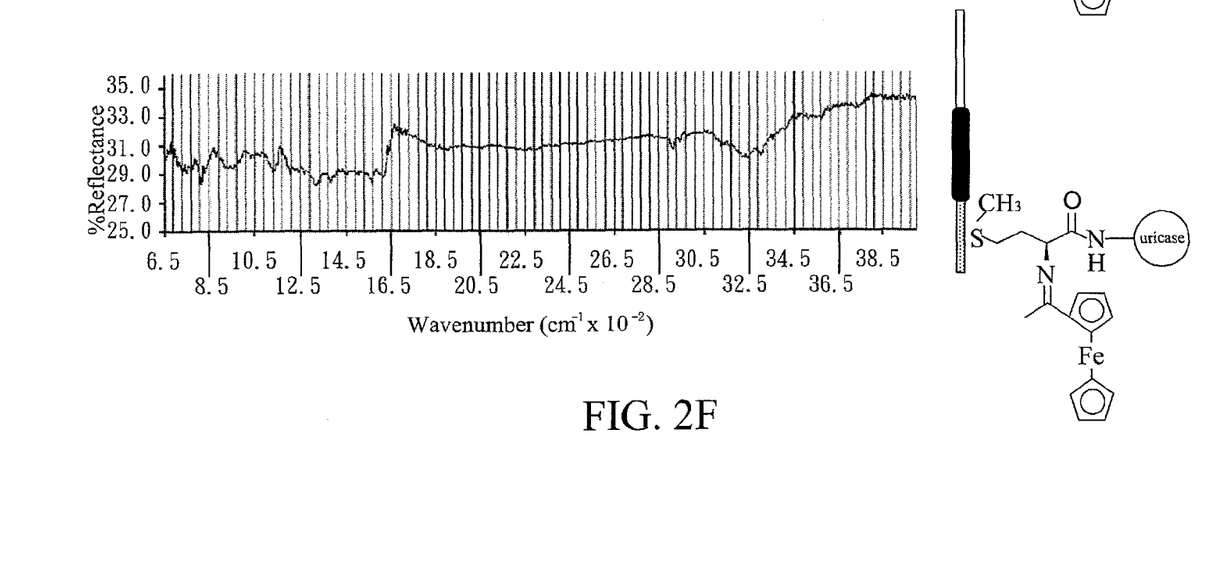
Figure 2G:
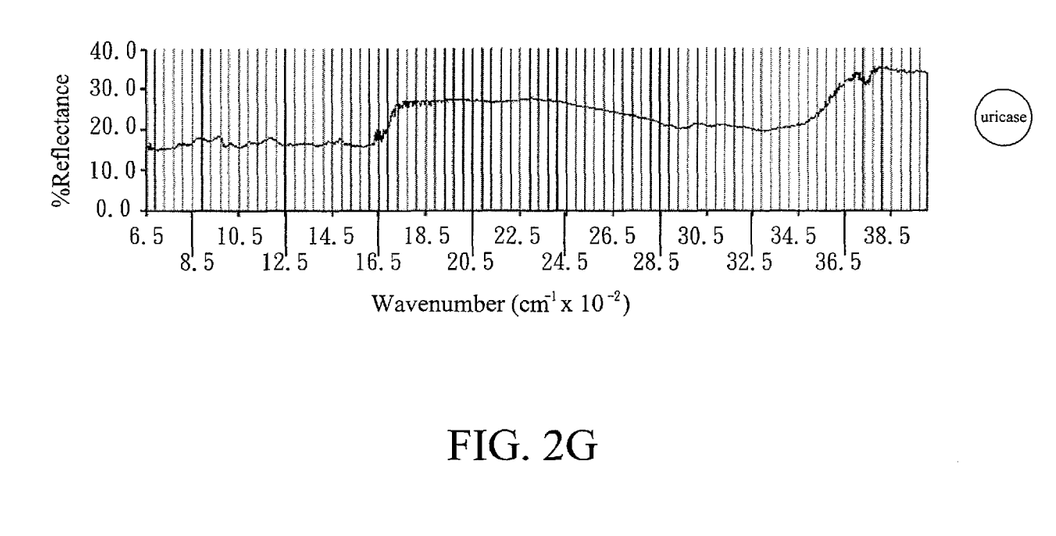

FIGS. 2A-2G step by step shows the Fourier transform infrared (FTIR) spectra of the formed uric acid-sensing electrode of the preferred embodiment. The FTIR reflection spectrometry can reflect characterization of chemical structure during each preparation step for the formed uric acid sensor electrode. The very weak reflectance peak around 2330 $cm^{-1}$ shown in the FTIR reflection spectrum of FIG. 2A was obtained from the naked copper lead of the polyimide enameled copper wire, and that very weak reflectance peak should be the vibration mode of isocyanates (R—N=C=O, near 2270 $cm^{-1}$) due to the polyimide residual left on the copper lead. FIG. 2B is a FTIR reflection spectrum after gold particles electrodeposited on the surface of naked copper wire, and there is no infrared signal. FIG. 2C is a FTIR reflection spectrum after the bonding of L-methionine to the gold particles, and the FTIR reflection spectrum indicates the strong C—H stretching vibration of alkane at 3000-2840 $cm^{-1}$, the methylene group (—$CH_2$—) bending vibration approximately 1465 $cm^{-1}$, the methyl group bending vibration approximately 1375 $cm^{-1}$, the strong stretching vibrations of the carboxylate salts (1600 $cm^{-1}$, asymmetry and 1400 $cm^{-1}$, symmetry), the broad N—H stretch of the amine salts (3300-2600 $cm^{-1}$), and the strong N—H bending vibration of primary amine salts (1610 $cm^{-1}$, asymmetry and 1500 $cm^{-1}$, symmetry) in L-methionine structure. FIG. 2D is a FTIR reflection spectrum after modifying the amino group of L-methionine with the aldehyde group of ferrocene carboxaldehyde (FcAld). The FTIR reflection spectrometry shown in FIG. 2D illustrates the characteristic stretching vibrations of the imine group ($R_2C$=N—R, 1690-1640 $cm^{-1}$) and the endo C=C double bond stretching (1650-1611 $cm^{-1}$) of ferrocene (Fc) ring. In addition, the =C—H out-of-plane bending of the Fc ring is in the range 1000-650 $cm^{-1}$. FIG. 2E is a FTIR reflection spectrum after the ester formation of N,N'-dicyclohexylcarbodiimide (DCC) with the carboxylic acid group of L-methionine. As shown in FIG. 2E, the characteristic structure brought from DCC shows that the C—N stretching vibration (1350-1000 $cm^{-1}$), the C—O stretching vibration (1300-1000 $cm^{-1}$), the imine group (1690-1640 $cm^{-1}$), and the C—H stretching vibration (3000-2840 $cm^{-1}$). On the other hand, the stretching vibrations of carboxylate salts (1600 $cm^{-1}$, asymmetry and 1400 $cm^{-1}$, symmetry) are weakened by the reaction. FIG. 2F is a FTIR reflection spectrum after uricase bound to the electrode. The FTIR reflection spectrum shown in FIG. 2F is characterized by the formation of an amide bond (—CO—NH—) acquired from the substitution of enzyme uricase for DCC and the peptide (amide) bond skeleton of the enzyme which are the C=O and N—H stretching vibration in the range 1680-1630 $cm^{-1}$ and 3475-3150 $cm^{-1}$, respectively. Also, the N—H bending vibration of the amide bond occurs around 1640-1550 $cm^{-1}$. FIG. 2G is a FTIR reflection spectrum of pure uricase powder. Compare the FTIR reflection spectrum of FIG. 2G and FIG. 2F, it is indeed verified again that the enzyme uricase had been successful bonded to the electrode.

Cyclic Voltammetry

Figure 3A:
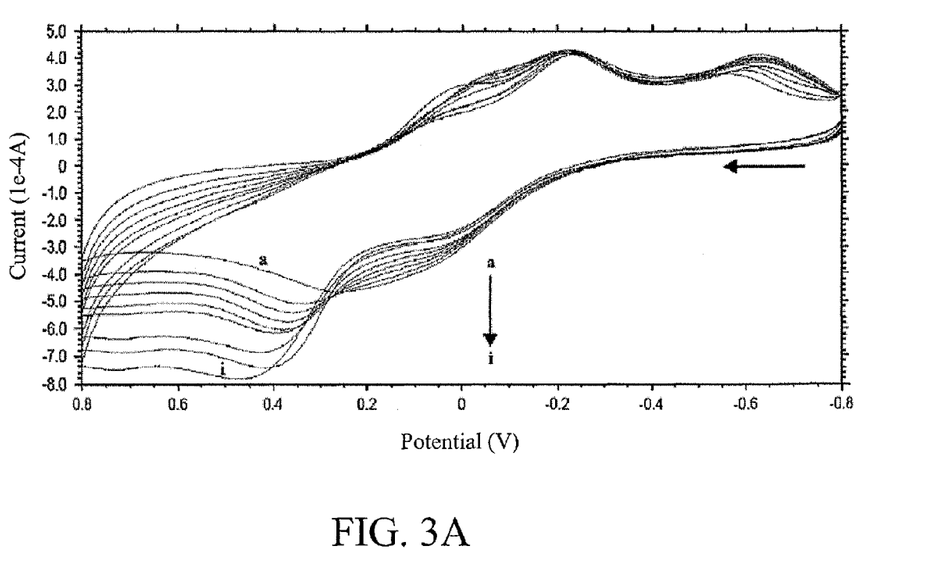
FIG. 3A shows the cyclic voltammograms of the produced uric acid-sensing electrode with nine different UA concentrations in 0.1 M pH 9.5 NaPB at 35° C.

The oxidation potential of the redox mediator FcAld chemically bonded on the produced electrode was measured by cyclic voltammetry (CV). The scan range of the potential was from −0.8 to 0.8 V with a scan rate of 50.0 mV $s^{-1}$. Nine different concentration levels (0.0, 0.595, 1.19, 1.79, 2.38, 2.98, 3.57, 4.17, and 4.76 mM) of the uric acid standard solution in 0.1 M pH 9.5 sodium phosphate buffer solution (NaPB) were measured with cyclic voltammetry at 35° C. FIG. 3A shows the cyclic voltammograms of the produced electrode respectively with the above nine different UA concentrations in 0.1 M pH 9.5 NaPB at 35° C. The cyclic voltammogram of the sodium phosphate buffer (NaPB) background solution indicates that the oxidation and reduction potential of mediator were 0.239 V and −0.232 V, respectively. The anodic current peak of mediator becomes broad and large accompanied by the increased oxidation at higher uric acid concentration. Also, as the concentration of uric acid increases the oxidation potential shifts from 0.239 V to 0.449 V. The cathodic and anodic current peak of the NaPB background solution at 0.044 V and −0.042 V, respectively, should be the corresponding oxidation and reduction of hydronium ion in solution which decreases as the uric acid concentration increases from cyclic voltammograms (a) to (i). The cathodic current peak of the NaPB background solution at −0.61 V could be the reduction of $H_2O$ that also decreases as the solution's UA concentration increases. The reduction of $H_2O$ produces $H_2$ and $OH^-$ which can be inhibited by the reduction of $H^+$ to $H_2$. However, the production of $OH^-$ neutralizes $H^+$ which makes the reduction current peak of $H^+$ decreases as UA concentration increases. It is also observed the appearance of bubbles at the platinum counter electrode during cyclic voltammetry. The reactions taking place at the working electrode are therefore suggested as of the following:

Uric acid+$2H_2O$+Uricase$_{(ox)}$→Allantoin+$CO_2$+$2H^+$+ Uricase$_{(red)}$

Uricase$_{(red)}$+2FcAld$^+$⇌Uricase$_{(ox)}$+2FcAld

2FcAld⇌2FcAld$^+$+$2e^-$

Standard Addition Calibration Curve

The performance of the produced uric acid-sensing electrode, such as the sensitivity, the limit of detection (LOD), and the linear dynamic uric acid concentration range, can be found from the standard addition calibration curve. The standard addition calibration curve of the electrode was prepared by the standard addition method at 35° C. [19].

The sodium phosphate buffer solution (NaPB) was deoxygenated by bubbling through nitrogen for 10 min before the standard addition then nitrogen was kept blowing on the solution surface during measurements. The uric acid stock solutions (4.76 mM) were prepared by 0.1 M pH 9.5 NaPB. Four milliliters of 0.1 M pH 9.5 NaPB were placed into the electrochemical cell as the background solution and magnetically stirred at 100 rpm. Then, a small volume (5.0-885.0 μL) of the UA standard solution was added every 40 s until a concentration of 2.38 mM was reached. The current for each standard addition was readout at the last 3 s of the standard addition. For higher concentrations of 2.98 mM, 3.57 mM and 4.76 mM, the current signal was separately measured by using external standards.

Figure 3B:
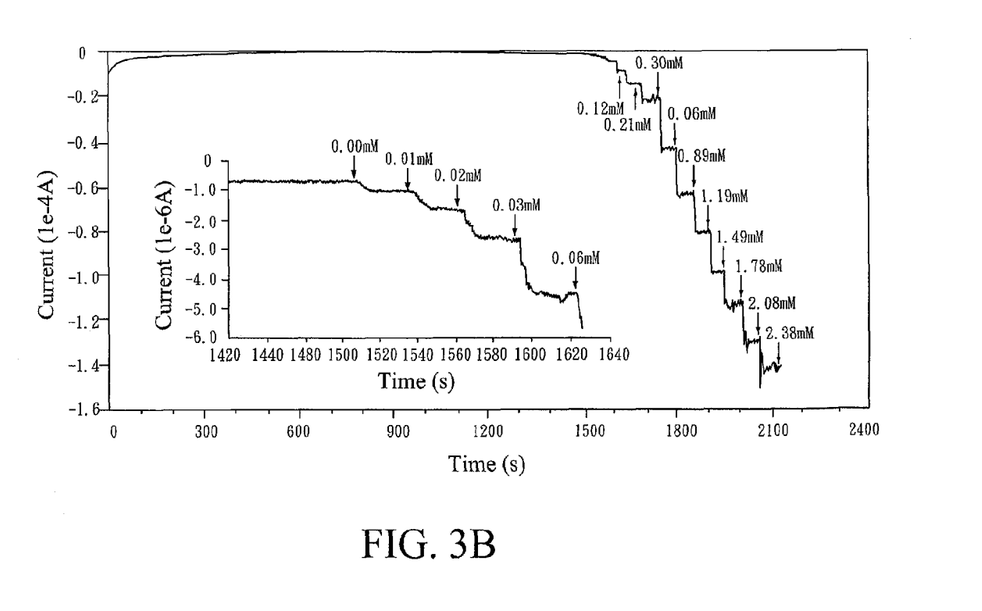
FIG. 3B is the standard addition current-time curve of uricase copper electrode which was made by the addition of a specific volume of uric acid (UA) standard solution into the sodium phosphate buffer solution (NaPB) that the current changes accompanied by the change of UA concentration during each UA standard addition as described before.

FIG. 3B is the standard addition current-time curve of uricase copper electrode which was made by the addition of a specific volume of UA standard solution into the sodium phosphate buffer solution (NaPB) that the current changes accompanied by the change of UA concentration during each UA standard addition as described before. The current did not change significantly during the first 1600 s with the addition of small amount of UA. Thus, this part of the current signals was enlarged as in the inset diagram of FIG. 3B. Due to the size of the electrode and the vessel, the UA concentration can be standard added was limited to 2.38 mM. Above this limit viz 2.98, 3.57, and 4.76 mM, the current was separately measured using individual external standards. The response time of the electrode for current measurement needed to reach a steady-state current was about 5 s after each addition of UA standard solution.

Figure 3C:
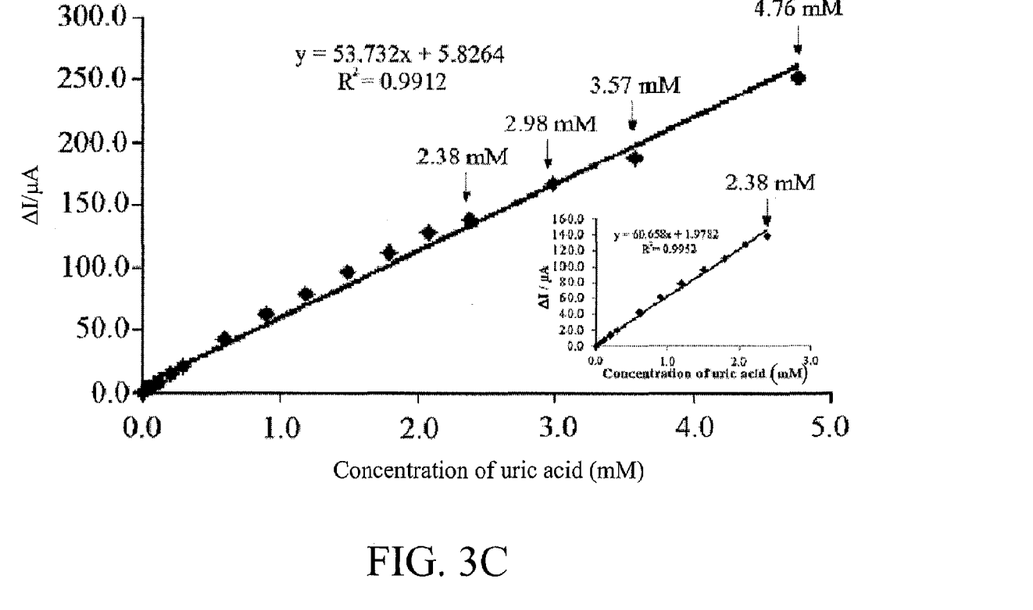
FIG. 3C shows the UA standard addition calibration curve of the produced electrode of the preferred embodiment.

FIG. 3C shows the UA standard addition calibration curve of the produced electrode of the preferred embodiment and this curve is obtained by the linear regression of the current signal versus the corresponding standard added UA concentration. The linear concentration range of the standard addition calibration curve was from 0 to 4.76 mM with very good linearity ($r^2=0.9912$). The limit of detection (LOD) of the produced was 6 μM obtained from standard addition calibration curve constituted by the five small UA standard concentrations (0.00, 0.01, 0.02, 0.03, and 0.06 mM).

Interference Effect

Four milliliters of 0.1 M pH 9.5 sodium phosphate buffer solution (NaPB) magnetically stirred at 100 rpm serve as the background solution. Then, 270 μL 4.76 mM UA standard solution prepared with 0.1 M pH 9.5 NaPB was added to the background solution to make a 0.3 mM standard concentration which mimics the normal level in human serum. The current signal of this standard uric acid solution was recorded. Subsequently, various 1 M interference standard solutions in 0.1 M pH 9.5 NaPB were prepared separately and added individually to one 0.3 mM UA standard solution to make the concentration of interference solutions from 0.1 to 5.0 mM. The total current signal of each of the interference solution was measured and compared to the current signal of the UA standard solution to obtain the signal ratio and the selectivity coefficient ($k_{uric\ acid,\ interference}$) as calculated by the following equations. The selectivity coefficient was used to show the degree of interference.

$$\text{Signal ratio} = (\text{Total signal})_{uric\ acid+interference}/(\text{Signal})_{uric\ acid}$$

$$k_{uric\ acid,\ interference} = (\text{Signal})_{interference}/(\text{Signal})_{uric\ acid}$$

Urine Sample Pretreatment

Urine specimens were collected from colleagues in the laboratory and then filtered through a porous Nylon membrane filter (47 mm, 0.22 μm pore diameter, Testhigh, Tienjin, China). Two milliliters of the filtered urine were diluted 10-fold with the working buffer (0.1 M, pH 9.5 NaPB). Four aliquots of 4 mL diluted urine were used for the UA quantification.

Quantification of Uric Acid in Urine Sample

Uric acid measurement for each urine specimens was tested by adding 40 μL of 4.76 mM standard UA solution every 40 s to 4 mL pretreated sample until the current signal was 1.5-3.0 times of the current signal of the unspiked urine sample. The spiked concentrations of UA after each sequential spiking of 4.76 mM UA standard solution are 0.047, 0.09, 0.14, and 0.18 mM, respectively. Then, the x-intercept of the linear standard addition calibration curve was found and the original UA concentration in the urine sample was determined by multiplying the x-intercept with the dilution factor. The standard deviation of the determined UA concentration was also calculated to understand the analysis precision.

The accuracy for the analysis of urinary UA using the produced electrode of the preferred embodiment was estimated by the recovery rate of the spike experiment. The diluted urine sample was spiked with standard UA solution about the same concentration of the diluted urine sample and the recovery rate of the added standard UA was determined by the standard addition method. The theoretical total UA concentration in the spiked urine sample ($[UA]_{theoretical\ total}$) and the measured total UA concentration of the spiked urine sample ($[UA]_{measured\ total}$) were determined separately. Then the following equation was used to calculate the accuracy.

$$\text{Accuracy} = 1 - |([UA]_{measured\ total}/[UA]_{theoretical\ total} - 1)| \times 100\%$$

Optimal Conditions of Amperometric Measurement

The optimal amperometric measurement pH of NaPB for the electrode was checked at the applied potential of 0.361 V by the calibration study of standard addition. The NaPB concentration was kept at 0.1 M and the pH of the NaPB was varied at 7.0, 7.5, 8.0, 8.5, 9.0, and 9.5 to measure the current signal of the UA standard solution at 0.3 mM (50 ppm). The measurement temperature was controlled at 35° C. Then, the analysis of variance (ANOVA) procedure together with the least significant test (LST) were applied for comparing the difference among the six measured currents, 6.71±0.83, 10.5±1.77, 10.3±3.75, 11.1±2.27, 12.1±1.82, 12.1±0.65 μA obtained for pH at 7.0, 7.5, 8.0, 8.5, 9.0 and 9.5, respectively. With the criteria of large current signal and small standard deviation, the results show that pH 9.5 was the best pH of the working buffer solution for UA amperometry measurements.

The optimal working temperature of the uricase electrode for UA measurement was tested at six different temperatures (15, 20, 25, 30, 35, and 40° C.) by keeping the solution's pH at 9.5. The obtained linear standard addition calibration curve in the same standard UA concentration range (0-1.19 mM) indicated the highest sensitivity (43.0 μA mM$^{-1}$) and the lowest LOD (0.003 mM) was at the working temperature 35° C. Therefore, the temperature 35° C. was used for the uric acid (UA) measurement.

Table 1 lists the interference effect of some potential compounds at different concentrations on the response of the produced electrode. The result shows that the degree of interference for urea (1.7 mM), lactic acid (0.5 mM), glucose (5.0 mM), creatinine (0.1 mM), and pyruvate (1.0 mM) was small (<15%) and for ascorbic acid (3.4 mM), cysteine (1.0 mM), glutamic acid (1.0 mM), histidine (1.0 mM), tyrosine (0.10 mM), DOPA (0.1 mM), and dopamine (0.1 mM), the degree of interference were great. However, taking consideration of the measurement error (the standard deviation of the data), there is no significant difference between the total signal of UA alone and the total signal of UA plus one of the following interference compounds: urea, lactic acid, glucose, cysteine, tyrosine, creatinine, and pyruvate by the t test that means there is no significant interference effect produced from these compounds. Although the interference effect of ascorbic acid, glutamic acid, histidine, DOPA, and dopamine were great, the concentration of these substances in human fluid is generally very low. Therefore, the interference for UA measurement in human urine specimens could be considerable small with the developed electrode by the present invention.

Long-Term Stability of Electrode

The long-term stability and reusability of the developed electrode by the present invention were demonstrated with the five performance parameters: the working oxidation potential, the sensitivity, the LOD, the response time, and the linear concentration range of the standard addition calibration curve and illustrated in FIGS. 4A-4E. The working oxidation potential of the electrode was obtained by cyclic voltammetry with 1.19 mM UA and the UA concentration range used for the standard addition procedure to construct the linear calibration curve to find other four parameters of the electrode was 0-2.38 mM. The electrode was tested once in a week and over a period of 209 days. After each testing, the electrode was stored with 0.1 M pH 7.0 NaPB in the refrigerator at 4° C. The variation of the working oxidation potential of the uricase electrode was shown in FIG. 4A. The potential was high at 0.361 V and 0.366 V during the beginning period for the freshly made electrode, then it gradually decreased and maintained at a value about 0.320 V after 100 days. Overall, the UA measurement potential was quite stable and low over the long-term testing period.

Figure 4A:
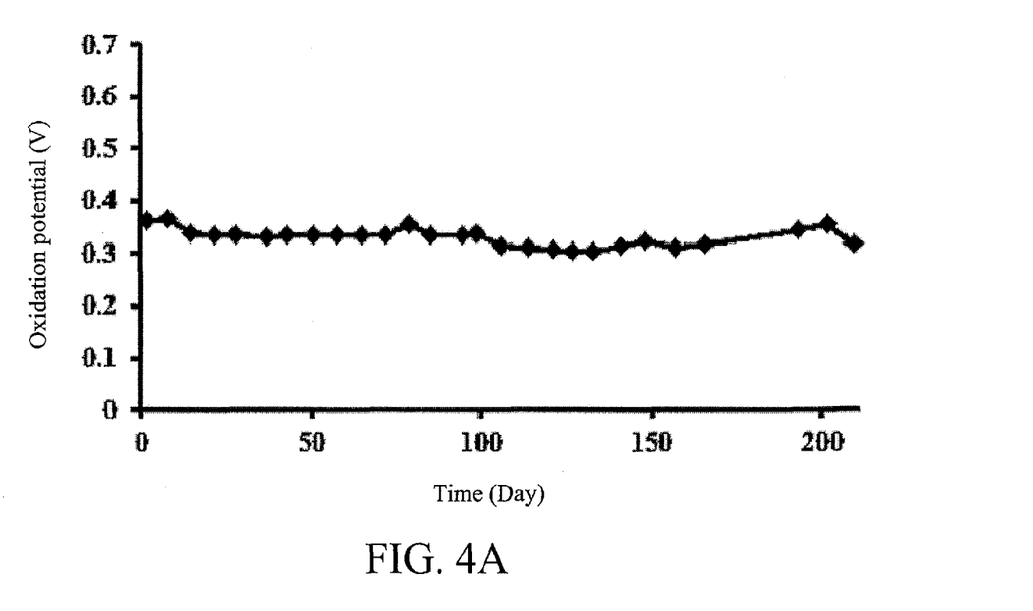
FIG. 4A, the working oxidation potential.
Figure 4B:
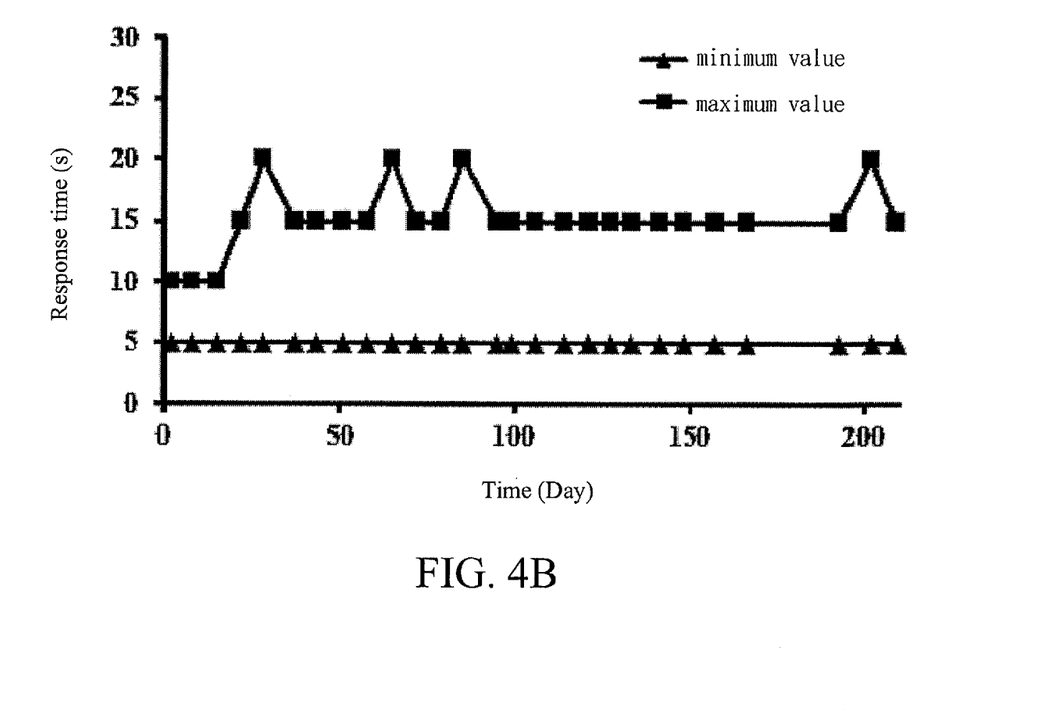
FIG. 4B, the sensitivity.

FIG. 4B shows that the response time of the produced electrode for UA measurement at low concentration around 0.60 mM was as fast as 5 s. However, at high UA concentration the measurement response time was 10 s for the freshly made electrode then it increased to 15 s and 20 s. Generally, the response time was quite stable and maintained a time at 15 s during most of the testing period.

Figure 4C:
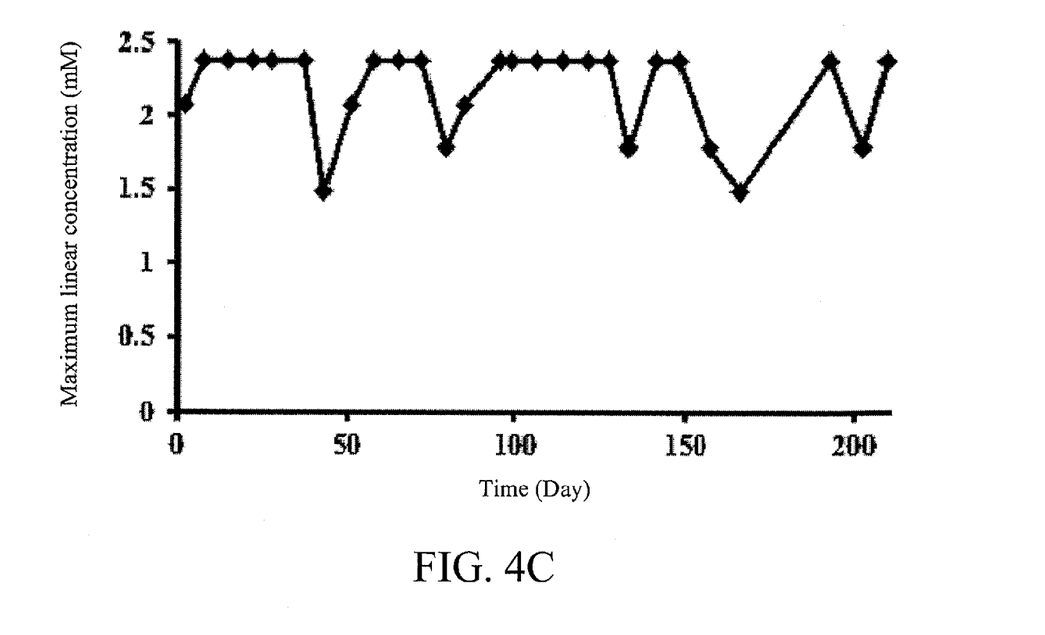
Figure 4D:
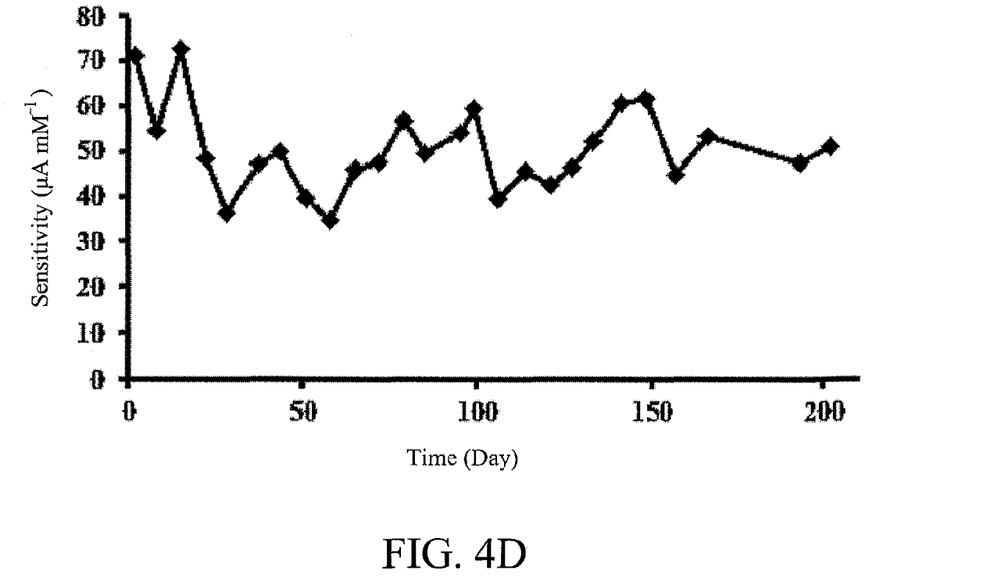
FIG. 4D, the response time.

FIG. 4C illustrates the variation of the maximum linear concentration of the linear standard addition calibration curve with the criteria of $r^2>0.995$. The results show that the maximum linear concentration can maintain at 2.38 mM during most of the time of the 209 days. The slope obtained from the linear standard addition calibration curves gives the measurement sensitivity of the electrode. FIG. 4D plots the variation of the sensitivity of the produced electrode, indicating that the electrode's sensitivity was all greater than 35 $pA\ mM^{-1}$ during the testing period and was high at 72.8 µA $mM^{-1}$ at the beginning period. Overall, the sensitivity varied around the value of 50 $pA\ mM^{-1}$.

Figure 4E:
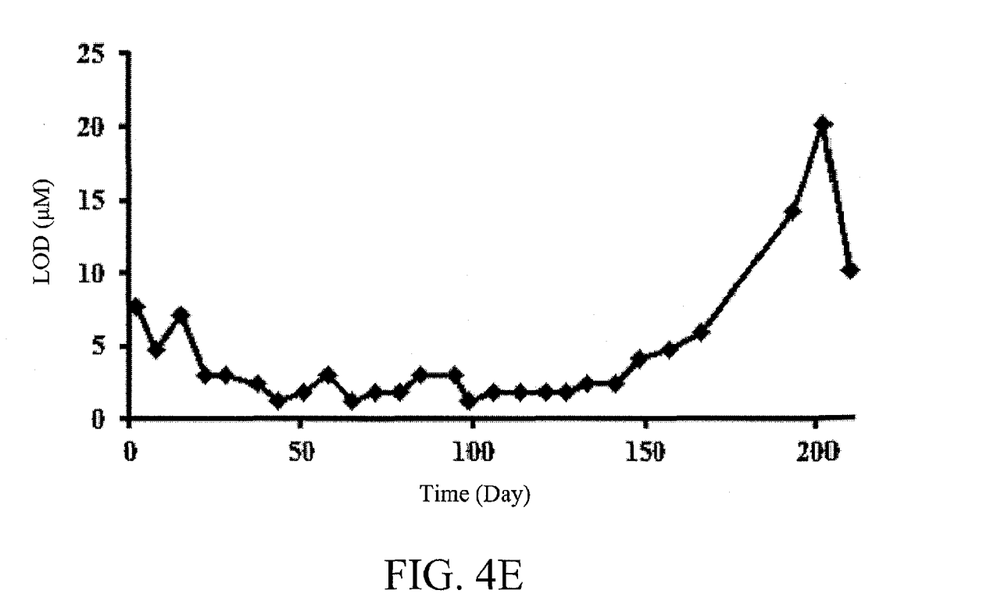
FIG. 4E, the linear concentration range.

FIG. 4E illustrates the variation of the limit of detection (LOD) of the produced electrode according to the preferred embodiment of the present invention. Although the LOD shown in FIG. 4E varies from 1.2 µM to 6.0 µM before the day of 166 days, most of the time the measured LOD maintains a value around 2.4 µM. After 170 days, the LOD rises to 20.2 µM and drops back to about 10 µM. Note that there seems not too much correlation between the sensitivity and the LOD of the electrode. The operational parameters such as stirring rate and temperature probably affect the LOD most. Generally, the detection limit of the electrode was quite good during the long-term testing. The electrode performance was also tested after 309 days and the electrode was still usable with a redox potential at 0.338 V, a response time of 5-15 s, the linear UA calibration concentration range of 0-1.78 mM ($r^2=0.9946$), a sensitivity of 77.6 $pA\ mM^{-1}$, and the LOD of 13.8 µM. All these evidence proved that the developed electrode can be long-term stably used without loss of uricase activity.

Table 2 lists the results of the determination of UA in four human urine specimens by using the produced electrode of the present invention and the standard addition method. The UA concentration varied from 0.380 mM to 2.860 mM. Since the relative standard deviations (RSDs) were all less than 2.5%, the determination of urinary UA by the developed electrode was very precise.

Table 3 lists the results of the analysis accuracy of the produced electrode. As shown in Table 3, the analysis accuracy determined by the spike recovery for the four urine specimens was all greater than 85.6% indicating quite accurate results. Therefore, the developed electrode is practical for urinary uric acid analysis.

Comparison of Electrode Performance

Table 4 list the compared result of electrode between the produced electrode of the present invention and other seven uric acid-sensing electrodes from the literatures. For the eight electrodes compared, three main electrode substrates have been utilized for the immobilization of uricase to fabricate the uricase electrode including polymer membrane [2], metal [5,15,20], the present invention, and carbon [4,7,21]. However, in recent advances, most of the electrodes are fabricated with composite materials to promote the electrode performance. The immobilization method of uricase can be either physical adsorption or chemical bonding but the majority of them without using redox mediator for substituting $O_2$ to oxidize the UA which not only needs higher redox potential for subsequent $H_2O_2$ oxidation but also subjects the variation of $O_2$ content to introduce large measurement error. Table 4 clearly shows that the redox potential was considerable lower for the two electrodes using ferrocene redox mediator for a direct oxidation of UA [7, the present invention]. In the preferred embodiment of the present invention, the redox mediator and uricase were both chemically bound to the electrode, the measurement response time was 5 s at low concentrations and 15 s at high concentrations which are very fast as compared with other electrodes. Table 4 also indicates that the produced electrode by the present invention has the widest linear UA concentration range (0.0-2.38 mM, $r^2 \geq 0.9952$) for the standard calibration curve, ideal LODs (~2.4 µM), and without losing sensitivity during the 209-day testing period. The long-term stability of the produced electrode of the present invention demonstrates that the reusability of the developed electrode is superior to other electrodes and is potential for long-term multiple clinical applications.

Although specific embodiments have been illustrated and described, it will be appreciated by those skilled in the art that various modifications may be made without departing from the scope of the present invention, which is intended to be limited solely by the appended claims.

TABLE 1

| Uric acid (mM) | Interferent | Interferent concentration (mM) | Total signal[a] (µA) | Signal ratio[b] | Interference signal (µA) | $k_{uric\ acid, interference}$[c] | Interference[d] |
|---|---|---|---|---|---|---|---|
| 0.3 | — | — | 10.88 ± 0.65 | 1.00 ± 0.08 | — | — | — |
| | Urea | 1.70 | 10.22 ± 0.31 | 0.94 ± 0.06 | −0.66 ± 0.72 | −0.06 | No |
| | Lactic acid | 0.50 | 9.44 ± 1.42 | 0.87 ± 0.14 | −1.45 ± 1.56 | −0.13 | No |
| | Glucose | 5.00 | 10.35 ± 1.19 | 0.95 ± 0.12 | −0.53 ± 1.36 | −0.05 | No |
| | Ascorbic acid | 3.40 | 132.09 ± 20.06 | 12.14 ± 1.98 | 121.21 ± 20.07 | 11.14 | Yes |
| | Glutamic acid | 1.00 | 7.08 ± 1.32 | 0.65 ± 0.13 | −3.80 ± 1.47 | −0.35 | Yes |
| | Cysteine | 1.00 | 13.35 ± 0.91 | 1.23 ± 0.11 | 2.47 ± 1.12 | 0.23 | No |
| | Histidine | 1.00 | 5.22 ± 0.83 | 0.48 ± 0.08 | −5.66 ± 1.05 | −0.52 | Yes |
| | Tyrosine | 0.10 | 8.67 ± 1.41 | 0.80 ± 0.14 | −2.21 ± 1.55 | −0.20 | No |
| | DOPA | 0.10 | 19.75 ± 0.61 | 1.82 ± 0.12 | 8.87 ± 0.89 | 0.82 | Yes |
| | Dopamine | 0.10 | 20.66 ± 1.00 | 1.90 ± 0.15 | 9.78 ± 1.19 | 0.90 | Yes |
| | Creatinine | 0.10 | 10.09 ± 0.23 | 0.93 ± 0.06 | −0.79 ± 0.69 | −0.07 | No |
| | Pyruvate | 1.00 | 10.13 ± 1.01 | 0.93 ± 0.11 | −0.75 ± 1.20 | −0.07 | No |

[a] Number of measurement (n) = 3.
[b] Signal ratio = (Total signal)$_{uric\ acid+interference}$/(Signal)$_{uric\ acid}$
[c] $k_{uric\ acid, interference}$ = (Signal)$_{interference}$/(Signal)$_{uric\ acid}$
[d] Using t test.

TABLE 2

| Urine sample | Linear equation | $R^2$ | Uric acid Concentration[a,b] (mM) | R.S.D. (%) |
|---|---|---|---|---|
| 1 | y = 4.6335x + 5.606 | 0.9957 | 1.210 ± 0.014 | 1.0 |
| 2 | y = 4.2219x + 5.5672 | 0.9984 | 1.320 ± 0.004 | 0.3 |
| 3 | y = 7.8348x + 3.0021 | 0.9951 | 0.380 ± 0.003 | 0.9 |
| 4 | y = 5.5772x + 15.933 | 0.9991 | 2.860 ± 0.067 | 2.4 |

[a] Number of measurement (n) = 4.

[b] standard deviation = $\dfrac{s_y}{|m|} \sqrt{\dfrac{1}{n} + \dfrac{y^2}{m^2 \sum (x_i - \bar{x})^2}}$

TABLE 3

| Urine sample | Measured uric acid concentration (mM) | Spike uric acid concentration (mM) | Theoretical total uric acid concentration (mM) | Measured total uric acid concentration (mM) | Recovery[a] (%) | Accuracy[b] (%) |
|---|---|---|---|---|---|---|
| 1 | 1.21 | 1.26 | 2.47 | 2.36 | 95.5 | 95.5 |
| 2 | 1.32 | 1.40 | 2.72 | 2.38 | 87.5 | 87.5 |
| 3 | 0.38 | 0.37 | 0.75 | 0.67 | 89.3 | 89.3 |
| 4 | 2.86 | 2.92 | 5.78 | 4.95 | 85.6 | 85.6 |

[a] Recovery = [UA]$_{Measured\ total\ uric\ acid}$/[UA]$_{Theoretical\ total\ uric\ acid}$
[b] Accuracy (%) = 1 − |[UA]$_{Measured\ total\ uric\ acid}$/[UA]$_{Theoretical\ total\ uric\ acid}$ − 1| × 100%

TABLE 4

| Electrode[a] | Enzyme immobilization method | Redox potential (V) | Response time (s) | Linear calibration range (mM) | LOD (µM) | Long-term reusability (d) | Reference |
|---|---|---|---|---|---|---|---|
| PANI | Chemical bonding | 0.4 | 60 | 0.1-0.6 | 10 | 126 | [2] |
| CS/uricase-PTBA-Pt$_{nano}$/Pt$_{plate}$/Au | Physical adsorption | 0.55 | 60 | 0.005-1.2 | 1 | 30 | [20] |
| PBNPs/c-MWCNT/PANI/Au | Physical adsorption | 0.4 | 4 | 0.005-0.8 | 5 | 210 | [5] |
| AuNPs/c-MWCNT/Au | Chemical bonding | 0.4 | 7 | 0.01-0.8 | 0.01 | 120 | [15] |
| Fc-GO/SPE | Physical adsorption | 0.3 | — | 0.001-0.02 | 0.1 | 10 | [7] |
| PB/SPE | Chemical bonding | −0.05[b] | 30 | 0.03-0.3 | 10 | 15 | [21] |
| PC/UOx/CA/CoPC/SPCE | Physical adsorption | 0.5 | 50 | 0.015-0.25 | 15 | Disposable | [4] |

TABLE 4-continued

| Electrode[a] | Enzyme immobilization method | Redox potential (V) | Response time (s) | Linear calibration range (mM) | LOD (μM) | Long-term reusability (d) | Reference |
|---|---|---|---|---|---|---|---|
| L-Met-FcAld/Au/Cu | Chemical bonding | 0.33[c] | 5-20 | 0.0-2.38[d] | 1.2-20.2 | 209 | The present invention |

[a]PANI: polyanailine; CS: chitosan; PTBA: poly(thiophene-3-bronic acid); PBNPs: Prussian blue nanoparticles; c-MWCNT: carboxylated multiwalled carbon nanotubes; Fc-GO: ferrocene-graphene oxide; SPE: screen-printed electrode; PC: polycarbonate; UOx: uricase; CA: cellulose acetate; CoPC: cobalt phthalocyanine; SPCE: screen-printed carbon electrode; L-Met-FcAld: L-methionine-ferrocene carboxaldehyde.
[b]For the reduction of $H_2O_2$.
[c]For 1.19 mM uric acid.
[d]Including the background buffer and with the criteria of $r^2 \geq 0.9950$.

What is claimed is:

1. A method for producing an electrode to detect uric acid, comprising the steps of:
   providing a metal substrate having a copper surface;
   forming a gold surface on the copper surface of the metal substrate and thus forming an electrode;
   modifying the gold surface by L-methionine to covalently bond the gold particles of the gold surface and a methylsulfanyl group of L-methionine, thereby forming a first modified electrode with a first modified surface;
   covalently bonding a redox mediator having an aldehyde group to an amino group of the L-methionine and thus resulting in a Schiff base, thereby forming a second modified electrode with a second modified surface, wherein the redox mediator comprises ferrocene carboxaldehyde;
   modifying the second modified surface by N,N'-dicyclohexylcarbodiimide, a carboxyl group of the L-methionine and N,N'-dicyclohexylcarbodiimide forms covalent bond, thereby forming a third modified electrode with a third modified surface; and
   contacting the third modified surface with an uricase, an amide bond being formed between a carboxyl group of L-methionine of the third modified surface and the uricase, thereby forming a fourth modified electrode with a fourth modified surface;
   whereby the fourth modified electrode has a response time of 5-15 seconds and a linear uric acid concentration range 0.0-2.38 mM with a linearity ($r^2$=0.9952) for a detecting standard calibration curve during a repeated use for 209 days, the fourth modified electrode being usable with a sensitivity about 50 μAM$^{-1}$ after repeated use for 209 days, the fourth modified electrode being usable with a limit of detection below 20.2 μM after repeated use for 209 days, and the fourth modified electrode having an accuracy 85.6-95.5% for human urine uric acid detection.

2. The method as recited in claim 1, wherein the metal substrate is made of metal.

3. An electrode for detecting uric acid in human urine, comprising:
   a substrate having a metal surface, wherein the metal surface is a copper surface;
   a gold surface formed on at least a portion of the metal surface;
   an L-methionine binding to the gold surface through its methylsulfanyl group;
   a redox mediator containing an aldehyde group, wherein the redox mediator and an amino group of the L-methionine form a Schiff base, and the redox mediator comprises ferrocene carboxaldehyde; and
   an uricase binding to L-methionine through a peptide-coupling reagent with a diimide structure, wherein the uricase and the peptide-coupling reagent form an amide bond, wherein the peptide-coupling reagent is N,N'-dicyclohexylcarbodiimide;
   whereby the electrode has a response time of 5-15 seconds and a linear uric acid concentration range 0.0-2.38 mM with a linearity ($r^2$=0.9952) for a detecting standard calibration curve during a repeated use for 209 days, the electrode being usable with a sensitivity about 50 μAM$^{-1}$ after repeated use for 209 days, the electrode being usable with a limit of detection below 20.2 μM after repeated use for 209 days, and the electrode having an accuracy 85.6-95.5% for human urine uric acid detection.

4. The electrode as recited in claim 3, wherein the electrode is usable with a redox potential about 0.33V after repeated use for 209 days.

* * * * *